United States Patent [19]

Kuehn

[11] 4,145,544

[45] Mar. 20, 1979

[54] PREPARATION OF ISOCYANURATES

[75] Inventor: Erich Kuehn, Wilmington, Del.

[73] Assignee: ICI Americas Inc., Wilmington, Del.

[21] Appl. No.: 819,237

[22] Filed: Jul. 27, 1977

[51] Int. Cl.$^2$ .......................................... C07D 251/34
[52] U.S. Cl. ..................................... 544/222; 544/193
[58] Field of Search ................................ 544/222, 193

[56] References Cited

U.S. PATENT DOCUMENTS

| 2,801,244 | 7/1957 | Balon .................................... 544/222 |
| 2,952,665 | 9/1960 | Bunge et al. ......................... 544/221 |
| 3,179,626 | 4/1965 | Beitchman ............................ 544/222 |
| 3,211,585 | 10/1965 | Meyer et al. .......................... 544/222 |
| 3,573,259 | 3/1971 | Argabright et al. .................. 544/222 |
| 3,631,000 | 12/1971 | Argabright et al. .................. 544/222 |
| 3,817,937 | 6/1974 | Argabright et al. .................. 544/222 |
| 4,059,610 | 11/1977 | Handa et al. ......................... 544/222 |

Primary Examiner—John M. Ford

[57] ABSTRACT

Disclosed is a process for the preparation of ethylenically unsaturated isocyanurates which comprises a first step of trimerizing an aromatic polyisocyanate in the presence of an isocyanate trimerization catalyst and an ethylenically unsaturated solvent wherein at least 20% by weight of the solvent is an ethylenically unsaturated polar solvent, to form an isocyanate-containing isocyanurate and a second step of reacting the isocyanate-containing isocyanurate with a monohydric alcohol containing a vinylidene group to form an ethylenically unsaturated isocyanurate. The resulting solution of an ethylenically unsaturated isocyanurate dissolved in an ethylenically unsaturated solvent may be cured to form resins having excellent high temperature resistant properties.

9 Claims, No Drawings

PREPARATION OF ISOCYANURATES

This invention relates to a process for the preparation of ethylenically unsaturated isocyanurates, to iscoyanurate compositions, and to isocyanurate polymers. More particularly, this invention relates to the preparation of ethylenically unsaturated isocyanurates having improved properties by trimerizing an aromatic polyisocyanate in a vinylidene solvent comprising at least about 20% by weight of a polar solvent containing a vinylidene group, to form an isocyanate-containing isocyanurate, and then reacting the isocyanate groups of the isocyanate-containing isocyanurate with the hydroxyl group of a monohydric alcohol containing a vinylidene group.

The expression "vinylidene group" when used in this application means the group characterized by the formula:

wherein the two free valence bonds are not both connected to the same carbon atom.

The expression "aromatic polyisocyanate" when used in this application means a compound containing at least 2 isocyanate groups each of which is attached directly to the carbon atom of an aromatic ring.

The expression "isocyanurate" means a compound containing the structure:

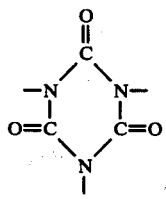

It has been found in accordance with the present invention that ethylenically unsaturated isocyanurates may be prepared by a two-step process which comprises a first step of trimerizing an aromatic polyisocyanate in the presence of an isocyanate trimerization catalyst and in the presence of a vinylidene solvent, wherein at least 20 weight percent of the solvent comprises an ethylenically unsaturated polar solvent, to form an isocyanate-containing isocyanurate and a second step of reacting the isocyanate-containing isocyanurate with a monohydric alcohol containing a vinylidene group to form an isocyanurate-containing urethane group and ethylenically unsaturated groups.

In carrying out the process of this invention, it is essential that the trimerization reaction in the first step and the urethane formation reaction in the second step be conducted in a vinylidene solvent wherein at least 20% by weight of the solvent is a polar solvent containing a vinylidene group. Attempts to use a solvent containing less than 20% by weight of a polar solvent, for example a blend of 9 parts of styrene and 1 part of ethylacrylate, result in the formation of gel and unworkable solids. There is no upper limit on the amount of polar solvent which may be used except that no advantage is obtained by the use of more than about 40% of polar solvent and polar solvents in general tend to be more expensive than non-polar solvents. Accordingly, it is preferred to carry out the reactions of the process of this invention in a solvent system comprising from 20% to 40% by weight of polar solvent. A particularly preferred solvent system comprises from 25% to 35% by weight of polar solvent.

The solvent used in the process of this invention should not contain any group which would react with the isocyanate groups or in any way interfere with the isocyanurate formation in step one or with the urethane formation in step two of the process. Thus, the solvent should not contain any hydroxyl, carboxyl, or amine groups which might interfere with these reactions. This restriction tends to limit the suitable solvents to esters, ethers, hydrocarbons and similar solvents containing non-reactive groups. Illustrative examples of polar solvents which may be used in the process of this invention include methylmethacrylate, ethylmethacrylate, ethylacrylate, 2-ethylhexylacrylate, 2-ethylhexylmethacrylate, butylacrylate, butylmethacrylate, cyclohexylmethacrylate, cyclohexylacrylate, vinyl acetate, tetrahydrofurfuryl methacrylate, diethyleneglycol diacrylate, triethyleneglycol diacrylate, allylmethacrylate, diallylfurmate, 1,3-butyleneglycol dimethacrylate, and propyleneglycol diacrylate. A preferred polar solvent is ethylacrylate.

Illustrative examples of non-polar solvents which may be used include styrene, divinylbenzene, chlorostyrene, acrylonitrile, vinyl toluene, and vinyl pyrrolidone. A preferred non-polar solvent is styrene.

While it is critical that the solvent used in the process of this invention must contain at least 20%, and preferably at least 25%, by weight of a polar solvent, the total amount of solvent employed may vary over a rather wide range. The particular amount of solvent used will depend somewhat, of course, on the nature of the solvent used and on the solubility of the reactants. The amount of solvent used will also depend, in the case of those solvents containing polymerizable double bonds, on the nature of the properties desired in the final product. Thus, if one is interested in preparing the ethylenically unsaturated isocyanurate of tolylene diisocyanate and hydroxypropylmethacrylate in a solvent comprising 3 parts of styrene and 1 part of ethylacrylate, the high temperature properties of the final product will increase as the concentration of the solvent decreases. In general, however, the amount of solvent used will be chosen so that the solvent comprises from 10% to 80% by weight, and preferably from 25% to 65% by weight, of the total composition. A particularly preferred amount of solvent comprises from 40% to 60% by weight of the total reaction mixture. The use of less than about 10% by weight of solvent is undesirable due to the formation of gels and insoluble solids and the use of more than about 80% of solvent tends to be needlessly expensive.

To assist in describing the invention so that it may be better understood by those skilled in the art, but without wishing to be bound by any particular theory, it is believed that the process of this invention wherein a monohydric alcohol and a aromatic diisocyanate are used, may be illustrated by the following equations:

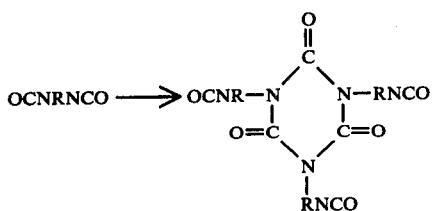

(1)

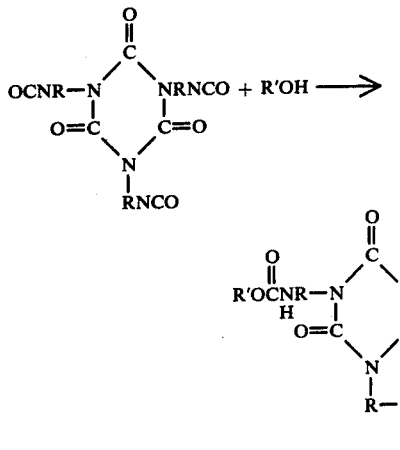

(2)

where R is a divalent radical obtained by removing two isocyanate groups from an aromatic diisocyanate and R' is a monovalent organic radical containing a vinylidene group.

The trimerization of the aromatic isocyanate in the first step of the process of this invention is preferably carried out by dissolving an aromatic isocyanate and a trimerization catalyst in an unsaturated solvent containing at least 20% by weight of a polar solvent and heating the resulting solution until the free isocyanate content has decreased to a level of from about 10% to about 18%. Above 18% NCO, large amounts of the aromatic polyisocyanate are still unreacted; below about 10% free NCO, there is a danger of forming a gelled product. It will be understood, of course, that if desired the trimerization in the first step may be terminated before the NCO content has decreased to 18% and it may be continued until the NCO content has decreased to below 10%. When the reaction is continued to an NCO content substantially below 10%, it may be necessary to increase the amount of polar solvent present and/or the total amount of solvent present. The temperature of the trimerization reaction should be maintained within a range from about 40° C. up to the boiling point of the solvent used. In most cases, a temperature from about 50° C. to 80° C. has been found to be satisfactory.

The concentration of the aromatic isocyanate in the solvent should be from about 10 to 80 weight percent and preferably from 40 to 60 weight percent. Lower concentrations are expensive and higher solid concentrations tend to gel and form unworkable solids.

The trimerization catalyst used in the first step of the process of this invention may be any compound which will catalyze the trimerization of aromatic isocyanates to form isocyanurates and which trimerization catalyst is also soluble in the solvent system employed herein. A preferred trimerization catalyst is a mixture of calcium naphthanate and zinc octoate. Illustrative examples of other trimerization catalysts which may be employed include: tertiary amines such as dimethylaniline, methylmorphline, triethylenediamine, triethylenetetraamine, tributylphosphate, N-benzyltrimethyl ammonium hydroxide, N,N-diethylethanolamine, 1,4-diazobycyclo-2,2,2(octane), and mixtures of tertiary amines.

The amount of trimerization catalyst which is used is comparatively small and depends upon the particular catalyst and aromatic diisocyanate selected. Usually amounts below 1% are sufficient for trimerization purposes.

In order to avoid premature polymerization of the polymerizable materials used in the process of this invention, a small amount of any of the conventional polymerization inhibitors, such as hydroquinone, methylether of hydroquinone, sulfur, thiourea, and the like may be incorporated in the reaction mixture.

The polyisocyanate used in the process of this invention may be any aromatic polyisocyanate. For example, the aromatic polyisocyanate may be saturated, unsaturated, monomeric or polymeric. The only requirements are that the aromatic polyisocyanate contain at least two aromatic isocyanate groups and be free of any groups which interfere with the trimerization of the isocyanate groups or in the reaction of the free isocyanate groups with the monohydric alcohol. Illustrative examples of aromatic polyisocyanates which are particularly useful in this invention include: 2,4-tolylene diisocyanate; 2,6-tolylene diisocyanate; m-phenylene diisocyanate; p-phenylene diisocyanate; 1,5-naphthalene diisocyanate; 1,6-hexamethylene diisocyanate; 4,4'-diphenyl ether diisocyanate; 4,4',4"-triphenylmethane triisocyanate; 4,4'-dimethyl-diphenyl methane-2,2',5,5'-tetraisocyanate; 2,4,4'-triisocyanate diphenyl methane; 2,4,6-triisocyanato diphenyl ether; 2,2',4-triisocyanate diphenyl ether; 2,2',4-triisocyanate diphenyl sulfide; 2,4,4'-triisocyanato diphenyl sulfide; 2,3',4-triisocyanato-4'-methyl diphenyl ether; 2,3',4-triisocyanato-4'-methoxy diphenyl ether; 2,4,4'-triisocyanato-3'-chlorodiphenylether; 4,4',6-diphenyl triisocyanato; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4'-diisocyanato diphenyl ether; 5,6-dimethyl-1,3-phenylene diisocyanate; benzidine diisocyanate; 9,10-anthraceine diisocyanate; 4,6-dimethyl-1,3-phenylene diisocyanate; 4,4'-diisocyanatodibenzyl; 3,3'-dimethyl-4,4'-diisocyanato diphenyl methane; 2,6-dimethyl-4,4'-diisocyanato diphenyl; 3,3'-dimethyl-4,4'-diisocyanato diphenyl; 3,3'-dimethoxy-4,4'-diisocyanato diphenyl; 1,4-anthracene diisocyanate; 1,8-naphthalene diisocyanate; 2,4,6-tolylene triisocyanate; 2,4,4'-triisocyanato diphenyl ether; diphenylmethane polyisocyanate available under the trademark Mondur MR having a functionality of 2.6; 1,3-xylene-4,6-diisocyanate; aromatic isocyanate terminated prepolymers of diols and triols; and aromatic isocyanate terminated prepolymers of polyesters. Preferred polyisocyanates are 2,4-tolylene diisocyanate, 2,6-tolylene diisocyanate, and mixtures thereof.

In the second step of the process of this invention, sufficient monohydric alcohol is added to the solution of the isocyanate-containing isocyanurate formed in step 1 in sufficient amounts so that all the NCO groups are reacted with hydroxyl groups to form urethane groups. In other words, the resulting unsaturated isocyanurate should be essentially free of isocyanate groups. The monohydric alcohol may be added direct to the solution of the isocyanate-containing isocyanurate or the monohydric alcohol may be first dissolved in additional vinylidene solvent and then added to the isocyanate-containing isocyanurate.

The monohydric alcohols which are useful in the process of this invention include any monohydric alochol containing a vinylidene group and which is free of a group, other than the hydroxyl group, which is reactive with isocyanate groups. A preferred class of monohydric alcohols are prepared by reacting a monocarboxcylic acid containing a vinylidene group with a dihydric alcohol. Illustrative examples of such acids include acrylic acid; methacrylic acid; ethacrylic acid; 9,12-octadecadienoic acid; 9,12,15-octadecatrienoic acid; 9,11,13-octadecatrienoic acid; and 4-keto-9,11,13-octacecatrienoic acid. Illustrative examples of dihydric alcohols include ethyleneglycol; propyleneglycol; diethyleneglycol; dipropyleneglycol; 1,3-butyleneglycol; 1,4-butyleneglycol; 2,3-butyleneglycol; pentamethyleneglycol; hexamethyleneglycol; neopentylglycol; di-($\beta$-hydroxyethyl)ether of hydroquinone; 4,4'-thiodiphenyl; dibromoneopentylglycol; dimethylhexenediol; dimethylhexanediol; 4-mercaptophenyl; 2-butene-1,4-diol; 2-butane-1,4-diol; 2,3-dibromo-2-butene-1,4-diol; 2,2,3,3-tetrachloro-1,4-butanediol; 2,2,4-trimethyl-1,6-hexanediol; 2,5-dimethyl-2,5-hexanediol; 2,2,4,4-tetramethyl-1,3-cyclobutanediol; 1,4-cyclohexanediol; 1,4-cyclohexanedimethanol; hydrogenated bisphenol A; and ethylene oxide and/or propylene oxide ethers of the above-mentioned diols. A preferred group of monohydric alcohols which are useful in the process of this invention comprises hydroxypropyl methacrylate, hydroxyethyl methracylate, hydroxyethyl acrylate, and hydroxypropyl acrylate.

The mere mixing of the monohydric alcohol and isocyanate-containing isocyanurate results in an exothermic reaction which in many instances generates sufficient heat for completion of the reaction. The reactants are maintained at an elevated temperature above ambient room temperature until the isocyanate content of the mixture is reduced to the point to indicate that the resulting unsaturated isocyanurate product is free of isocyanate groups. In general, it is preferred to conduct the reaction of the monohydric alcohol with the isocyanate-containing isocyanurate at temperatures between 25° C. and 110° C., and preferably from about 80° C. to about 95° C. Although a catalyst is not required in this reaction, the reaction may be carried out in the presence of a catalyst which promotes the reaction of isocyanate groups with hydroxyl groups, for example, in the presence of a cupric salt, such as cupric acetate as taught in British Pat. No. 629,015.

To improve the storage stability of the solutions, from about 0.01% to about 0.2% by weight of a polymerization inhibitor, such as tertiary butylcatechol or hydroquinone may be employed. Other additives which may also be added to the solution include, for example, antioxidents, UV obsorbers, dyes, pigments, fillers, and plasticizers.

The ethylenically unsaturated isocyanurate solutions of this invention may be polymerized alone or in combination with other ethylenically unsaturated compounds. In order to accomplish such polymerization within a reasonable time, a suitable reaction initiator, of the kind frequently referred to as "free radical catalysts," may be used to promote the polymerization reaction. Exemplary of such catalysts are organic peroxides such as methyl ethyl ketone peroxide, benzoyl peroxide, t-butyl perbenzoate, cumene hydroperoxide, and succinic peroxide; redox catalysts; and ammonium persulfate. Accelerators for the polymerization reaction may also be used. Exemplary of such accelerators are dimethyl aniline and cobalt naphthenate.

Polymers of the isocyanurate products produced by the process of the present invention have been found to be particularly useful in applications such as castings, coatings, and laminates where it is desirable to have improved high temperature properties, they are also useful in the preparation of a variety of filament wound products such as pipes, ducts, and storage tanks and in molded products where they may be combined with fillers and fibers.

In order to describe the present invention so that it may be more clearly understood, the following examples are set forth. These examples are provided primarily for the purpose of illustration and any enumeration of details contained therein should not be interpreted as a limitation of the concept of the present invention. All parts and percentages are by weight unless otherwise specified.

Castings are prepared by pouring the resin composition into a mold comprising two glass plates each of which had previously been coated with a mold-releasing agent, spaced $\frac{1}{8}$ inch apart, and sealed together on three edges. After the composition is poured into the mold, the fourth edge is sealed and the composition is allowed to cure at room temperature for 24 hours. At the end of this time, the material is post cured by placing the mold in an oven at 100° C. for 4 hours. After cooling, the glass plates were separated and the solid casting is removed and tested.

Tensile strength is measured in accordance with A.S.T.M. Standard D-638-71a.

Flexural strength is measured in accordance with A.S.T.M. Standard D-790-71.

Elongation is measured in accordance with A.S.T.M. Standard D-638-71a.

Heat distortion temperature (HDT) is measured in accordance with A.S.T.M. Standard D-648-72.

Charpy impact is determined in accordance with A.S.T.M. Standard D-256.

EXAMPLE 1

To a 1-liter reaction vessel equipped with stirrer, nitrogen inlet, thermometer, condenser, and dropping funnel, are added 200 grams tolylene diisocyanate, 120 grams styrene, 80 grams ethylacrylate, and 0.1 gram hydroquinone. The resulting solution mixture is heated to 70° C., and 1.76 grams of calcium napthanate and 0.73 gram of zinc octoate are added while maintaining the mixture at 70° C. The reaction mixture is maintained at 70° C. until the isocyanate content has decreased to 13.29%. The temperature is then lowered to 50° C. and 157 grams of styrene are added. Then from a dropping funnel, 170.64 grams of hydroxyethylmethacrylate are added at such a rate that the exotherm does not exceed 70° C. After all the hydroxyethylmethacrylate has been added, the reaction temperature is maintained at 70° C. for 1 hour and 0.35 gram hydroquinone and 0.35 gram tin octoate are added. The reaction mixture is maintained at 70° C. until the isocyanate content is essentially zero. 5 grams of hydroxyethylmethacrylate are then added to react with any residual NCO groups which might be present in the product. The resulting product is a 50% solution of unsaturated isocyanurate dissolved in the vinylidene monomer and at room temperature has a viscosity of 9700 centipoises. The solution is slightly yellow and has a light haze. A casting is prepared from 350 grams of this solution, 5.6 grams of Lupersol DDM (60% solution of methyl ethyl ketone peroxide in dimethyl phthalate), 2.8 grams of cobalt naphthenate, and 0.7 gram of a 10% solution of t-butyl catechol in styrene. The properties of the casting are shown in following Table I.

EXAMPLE 2

To a 1-liter reaction kettle equipped with stirrer, nitrogen inlet, thermometer, condenser, and dropping funnel, are added 200 grams of tolylene diisocyanate, 140 grams of styrene, 60 grams of ethylacrylate, and 0.1 gram of hydroquinone and the mixture is heated to 70° C. 1.76 grams of calcium naphthanate and 0.73 gram of zinc octoate, and 0.66 gram of phenol are added to the reaction mixture and the mixture maintained at 70° C. until the NCO content has decreased to 14.74%, the reaction product is cooled to 50° C. and 100 grams of styrene are added. Then 189.1 grams of hydroxyethylmethacrylate are slowly added so that the exotherm does not exceed 70° C. The reaction mixture is then held at 70° C. for 1 hour and then 73.5 grams of styrene along with 0.37 gram hydroquinone and 0.37 gram tin octoate are added. The reaction mixture is then held at 70° C. until the total reaction time is 8 hours. At this point the NCO content is 0.29% and the reaction is quenched by the addition of 5 grams of hydroxyethylmethacrylate. The resulting solution has a viscosity of 6240 centipoises at room temperature. To 350 grams of this resin solution are added 5.6 grams of Lupersol DDM, 2.8 grams of cobalt naphthenate, and 1.4 grams of a 10% solution of t-butyl catechol in styrene, and the resulting composition used to prepare castings. The castings have the properties indicated in attached Table I.

EXAMPLE 3

To a 1-liter reaction vessel equipped as described in Example 1 are added 1350.0 grams of tolylene diisocyanate, 945.0 grams of styrene, 405.0 grams of ethylacrylate, and 0.68 gram of hydroquinone and heated to 70° C. The reaction mixture is held at 70° C. until the isocyanate content has decreased to 17.2% to form an isocyanurate-containing polymerized toluenediisocyanate. 650 grams of this solution are charged to a 2-liter flask together with 0.52 gram of hydroquinone and 383.3 grams of styrene. The resulting mixture is stirred and 399.29 grams of hydroxypropyl methacrylate are added over a 20-minute period. The reaction mixture is then maintained at 75° C. for 5 hours at which point the NCO content is 0.48%. 22 grams of hydroxyethyl methacrylate are added and the solution diluted with styrene to form a 40% dissolved solid solution. 50 grams of this solution are mixed with 0.4 gram of cobalt naphthenate and 0.8 gram of Lupersol DDM and used to prepare a casting. The properties of the casting are given in Table I.

EXAMPLE 4

650 grams of the polymerized tolylene diisocyanate having an isocyanate content of 17.2% prepared in Example 3 are added to a two-liter glass flask together with 0.52 gram hydroquinone, 345.65 grams styrene, and 360.05 grams of hydroxypropyl methacrylate. The reaction mixture is heated at 70° C. to 75° C. for 6 hours at which time the NCO content had decreased to 0.48%. 20.81 grams of hydroxyethyl methacrylate are then added to react with the residual free isocyanate groups. The resulting amber solution had a viscosity of 584 centipoises at room temperature. To 300 grams of this solution are added 2.4 grams of cobalt naphthenate, 1.2 grams of a 10% solution of t-butyl catechol in styrene, and 4.8 grams of Lupersol DDM, and the resulting composition used to prepare a casting. The properties of the casting are shown in following Table I.

EXAMPLE 5

To the reaction vessel described in Example 1 are added 200.0 grams of tolylene diisocyanate, 120.0 grams of styrene, 80.0 grams of ethylacrylate, and 0.1 gram of hydroquinone. The resulting mixture is heated to 70° C. and 1.76 grams of calcium naphthanate and 0.73 gram of zinc octoate and 0.66 gram of phenol are added and the reaction temperature is maintained at 70° C. until the isocyanate content is 14.85%. 130 grams of the resulting solution are added to a 1-liter glass flask together with 0.3 gram hydroquinone and 607 grams of a 50% styrene solution of the monoester of methacrylic acid and polyoxypropylene(2)tetrabromobisphenol A. The reaction mixture is held at 75° C. for 5 hours after which time the NCO content is 0.67%. The reaction is quenched by the addition of 25 grams of hydroxyethyl methacrylate. To 350 grams of this solution are added 2.1 grams of dimethylaniline and 8.4 grams of Luperco ATC paste (50% solution of benzoyl peroxide in tricresyl phosphate). A casting is prepared from this solution and found to have the properties indicated in following Table I.

TABLE I

| Example No. | 1 | 2 | 3 | 4 | 5 |
|---|---|---|---|---|---|
| Flexural Strength, psi | 20,400 | 22,200 | 19,400 | 20,400 | 17,300 |
| Flexural Modulus | 0.54 | 0.55 | 0.44 | 0.47 | 0.51 |
| Barcol | 43–45 | 45–47 | 32–38 | 42–45 | 30–33 |
| Tensile Strength, psi | 12,200 | 11,400 | 10,600 | 12,000 | 10,800 |
| Tensile Modulus | 0.54 | 0.54 | 0.46 | 0.47 | 0.50 |
| % Elongation | 2.91 | 2.60 | 4.75 | 4.33 | 3.06 |
| HDT, ° C. | 120 | 120 | 93 | 91 | 81 |
| Charpy Impact | 4.45 | 4.95 | 6.21 | 4.14 | — |

EXAMPLE 6

1350.00 grams of tolylene diisocyanate, 945.00 grams of styrene, 405.00 grams of ethyl acrylate, and 0.68 gram of tequinol are added to a reaction kettle equipped with stirrer, nitrogen inlet, thermometer, condenser, and dropping funnel and heated to 70° C. 11.88 grams of calcium naphthenate (4% Ca), 4.93 grams of zinc octoate (8% Zn), and 4.46 grams of phenol are added to the reaction mixture and the temperature of the mixture is maintained at 70°–75° C. until the isocyanate content has decreased to 15.93%. 800 grams of the reaction mixture is then diluted with 379 grams of styrene. 0.6 gram of hydroquinone is added. 411 grams of hydroxyethyl methacrylate (96%) are added slowly at such a rate that the temperature of the reaction mixture does not exceed 70° C. The reaction mixture is held at a temperature of 70°–75° C. for 4 hours, at which time the isocyanate content is essentially zero. The reaction product contains 50% dissolved solids and has a viscosity of 896 cps at room temperature.

50 grams of the reaction product are mixed with 0.8 gram of Lupersol DDM, 0.4 gram cobalt naphthenate, and 0.2 gram of a 10% solution of t-butyl catechol in styrene. A gel time of 20 minutes and a peak exotherm of 175° C. is observed.

A standard two-ply laminate is prepared with 259 grams of chopped glass mat, 19 grams of C-glass surfacing veil, 920 grams of the 50% resin solution, 7.36 grams cobalt naphthenate, 5.52 grams of a 10% solution of t-butyl catechol in styrene, and 14.72 grams of Lupersol DDM. The resin has excellent glass wet-out properties. The laminate is cured for 24 hours at room temperature and for 4 hours at 100° C. The cured laminate contains 28.42% glass and has the following properties: flexural strength 19,500 psi; flexural modulus $0.89 \times 10^6$; Barcol hardness 52-60; tensile strength 14,100 psi; tensile modulus $1.12 \times 10^6$; and 1.48% elongation.

Although the process of this invention has been described with reference to specific reaction conditions and reactants, it will be apparent that still other different and equivalent reactants and process conditions may be substituted for those specifically described, all within the sphere and scope of this invention.

Having described the invention, what is claimed and desired to be secured by Letters Patent is:

1. In a process for preparing an ethylenically unsaturated isocyanurate which comprises
   (1) a first step of trimerizing an aromatic polyisocyanate to form an NCO-containing isocyanurate, said trimerizing being conducted in the presence of an isocyanate trimerization catalyst and in the presence of a solvent, and
   (2) a second step of reacting the NCO groups present in the NCO-containing isocyanurate with the hydroxyl group of a monohydric alcohol containing a vinylidene group, in the presence of a solvent to form an ethylenically unsaturated isocyanurate,
   the improvement comprising using as the solvent in steps (1) and (2) a vinylidene solvent which is free of a group reactive with an isocyanate group and which comprises at least 20 weight percent of an ethylenically unsaturated polar solvent.

2. A process of claim 1 wherein the monohydric alcohol is hydroxypropylmethacrylate, hydroxypropylacrylate, hydroxyethylmethacrylate, hydroxyethylacrylate, or mixtures thereof.

3. A process of claim 2 wherein the aromatic polyisocyanate is tolylene diisocyanate.

4. A process of claim 1 wherein the NCO content at the end of the first step is from about 10% to about 18% by weight, based on the total weight of solution.

5. A process of claim 4 wherein the vinylidene solvent comprises from 25% to 100% by weight of a polar solvent containing a vinylidene group and from 75% to 0% by weight of a non-polar solvent containing a vinylidene group.

6. A process of claim 5 wherein the vinylidene solvent is a blend of from 20% to 40% by weight of a polar solvent selected from the group consisting of ethylmethacrylate, ethylacrylate, 2-ethylhexylacrylate, 2-ethylhexylmethacrylate, butylacrylate, butylmethacrylate, cyclohexylmethacrylate, cyclohexylacrylate, vinyl acetate, tetrahydrofurfuryl methacrylate, diethylene glycol diacrylate, triethylene glycol diacrylate, allyl methacrylate, diallyl fumarate, 1,3-butylene glycol dimethacrylate, propylene glycol diacrylate, and mixtures thereof and from 80 to 60 parts by weight of a non-polar solvent selected from the group consisting of styrene, divinyl benzene, chlorostyrene, acrylonitrile, vinyl toluene, vinyl pyrrolidone, and mixtures thereof.

7. A process of claim 6 wherein the polar solvent is ethylacrylate and the non-polar solvent is styrene.

8. A process of claim 6 wherein the solvent contains from 25% to 35% by weight of polar solvent.

9. A process of claim 4 wherein the aromatic polyisocyanate is tolylene diisocyanate and the monohydric alcohol is hydroxypropylmethacrylate, hydroxypropylacrylate, hydroxyethylmethacrylate, hydroxyethylacrylate, or mixtures thereof.

* * * * *

UNITED STATES PATENT AND TRADEMARK OFFICE
CERTIFICATE OF CORRECTION

PATENT NO. : 4,145,544
DATED : March 20, 1979
INVENTOR(S) : Erich Kuehn

It is certified that error appears in the above–identified patent and that said Letters Patent are hereby corrected as shown below:

Column 1, Line 21 correct -- $CH_2=C>$ -- $CH_2=C<$

Signed and Sealed this

Eighth Day of April 1980

[SEAL]

Attest:

SIDNEY A. DIAMOND

Attesting Officer — Commissioner of Patents and Trademarks